United States Patent
Habenstein

[11] Patent Number: 6,114,170
[45] Date of Patent: *Sep. 5, 2000

[54] REAGENT FOR DETERMINING THE IONIC STRENGTH AND/OR THE SPECIFIC WEIGHT OF AQUEOUS LIQUIDS AND METHOD

[75] Inventor: Klaus Habenstein, Wetter, Germany

[73] Assignee: Dade Behring Marburg GmbH, Germany

[*] Notice: This patent is subject to a terminal disclaimer.

[21] Appl. No.: 08/950,981

[22] Filed: Oct. 15, 1997

Related U.S. Application Data

[63] Continuation of application No. 08/364,422, Dec. 27, 1994, Pat. No. 5,858,788, which is a continuation of application No. 07/883,128, May 14, 1992, abandoned.

[30] Foreign Application Priority Data

May 17, 1991 [DE] Germany ............................... 41 16 108

[51] Int. Cl.[7] ............................... G01N 33/50; G01N 9/00
[52] U.S. Cl. ............................... 436/2; 436/163; 436/166; 436/169; 422/56; 422/57; 73/32 R; 73/64.54
[58] Field of Search ........................... 422/56, 57; 436/66, 436/74, 79, 2, 163, 166, 169; 73/32 R, 64.54

[56] References Cited

U.S. PATENT DOCUMENTS

| | | | |
|---|---|---|---|
| 4,015,462 | 4/1977 | Greyson et al. | 73/32 R |
| 4,318,709 | 3/1982 | Falb et al. | 436/163 |
| 4,473,650 | 9/1984 | Wang | 436/163 X |
| 4,532,216 | 7/1985 | Wang | 422/56 X |
| 4,822,743 | 4/1989 | Wegrzyn | 436/3 |
| 4,853,338 | 8/1989 | Benezra et al. | 436/66 |
| 4,935,342 | 6/1990 | Seligson et al. | 436/17 X |
| 5,055,407 | 10/1991 | Lau et al. | 422/57 X |
| 5,064,615 | 11/1991 | Mangold et al. | 422/56 |
| 5,106,752 | 4/1992 | Mangold et al. | 430/163 X |
| 5,215,924 | 6/1993 | Rittersdorf et al. | 436/164 X |
| 5,565,363 | 10/1996 | Iwata et al. | 436/2 |

FOREIGN PATENT DOCUMENTS

| | | |
|---|---|---|
| 0 023 631 A1 | 2/1981 | European Pat. Off. . |
| 0 114 315 A2 | 8/1984 | European Pat. Off. . |
| 0 349 934 A2 | 1/1990 | European Pat. Off. . |
| 29 44 980 A1 | 5/1980 | Germany . |
| 59-120843 | 7/1984 | Japan . |

OTHER PUBLICATIONS

Yamamoto et al, "Spectrophotometric method for the determination of ionic surfactants by flow–injection analysis with acidic dyes", Analytica Chimica Acta, 246 (1991), pp. 333–339, 1991.

Roempps Chemi Lexikon, 7th. Edition, vol. 5, p. 3399–3400, date unknown.

Roempps Chemie Lexikon, 7th. Edition, vol. 6, p. 4153–4157, date unknown.

*Primary Examiner*—Maureen M. Wallenhorst
*Attorney, Agent, or Firm*—Finnegan, Henderson, Farabow, Garrett & Dunner, L.L.P.

[57] ABSTRACT

The invention relates to a method for determining the ionic strength and/or the specific weight of aqueous liquids and a reagent for this purpose, the composition of the reagent being such that the color change indicating the ionic strength is essentially directly dependent on the specific weight of the liquid to be determined and not on a pH shift.

17 Claims, 1 Drawing Sheet

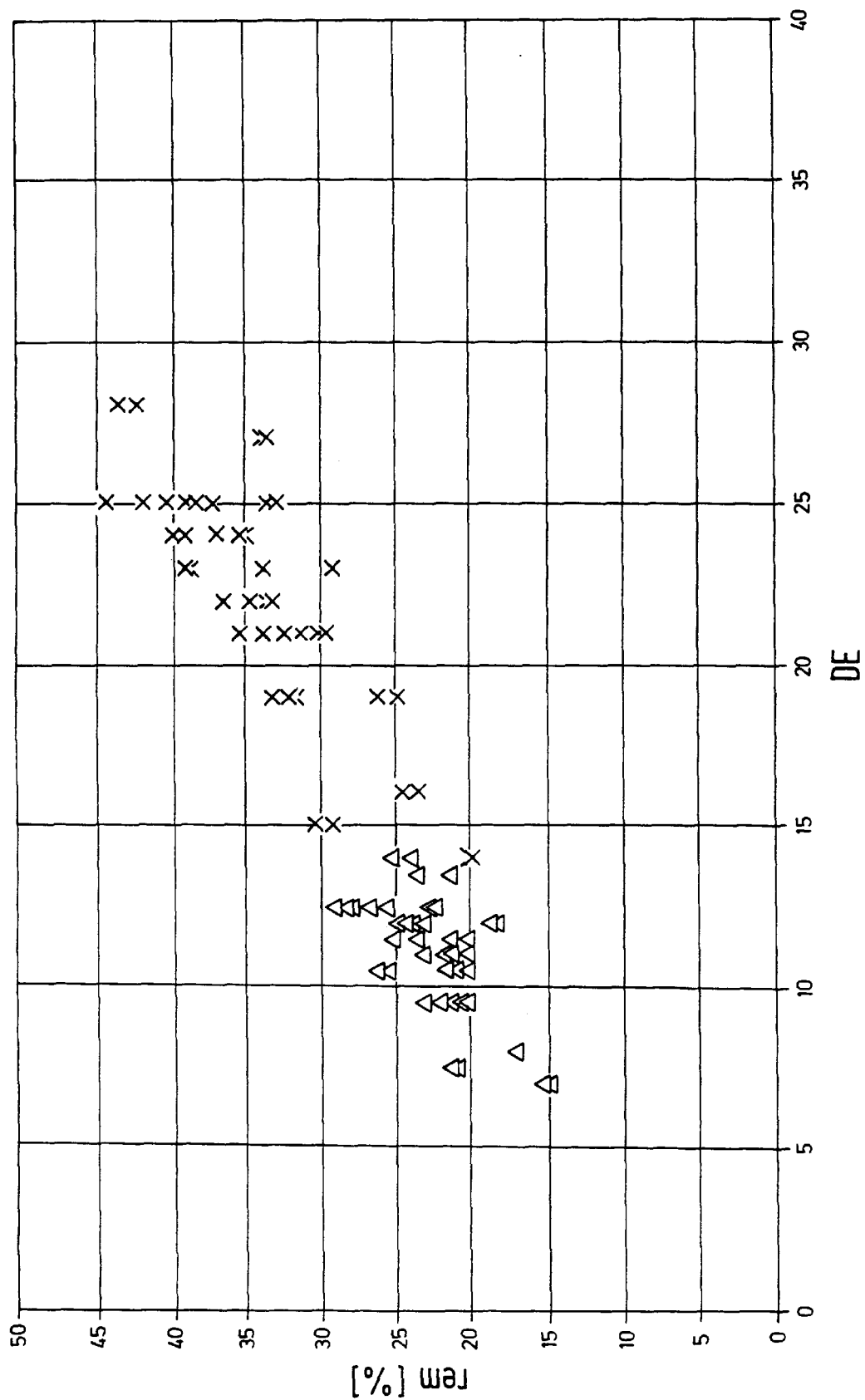

REAGENT FOR DETERMINING THE IONIC STRENGTH AND/OR THE SPECIFIC WEIGHT OF AQUEOUS LIQUIDS AND METHOD

This is a continuation of application Ser. No. 08/364,422, filed Dec. 27, 1994 now U.S. Pat. No. 5,858,788 issued Jan. 12, 1999, which is a continuation of Ser. No. 07/883,128, filed May 14, 1992 now abandoned.

FIELD OF THE INVENTION

The invention relates to a method for determining the ionic strength and/or the specific weight of aqueous liquids and a reagent for this purpose, the composition of the reagent being such that the color change indicating the ionic strength is essentially directly dependent on the specific weight of the liquid to be determined and not on a pH shift.

DESCRIPTION OF THE RELATED ART

The specific weight of a liquid can be determined in different ways using various auxiliary equipment, for example using hydrometers, pycnometers or refractometers. It is true that the measuring accuracies which can be achieved are, without exception, good, but from time to time there are complicated calibration and temperature adjustment or cleaning tasks associated with these equipment-related measuring methods. In particular for series or serial investigations, such methods can therefore only be employed and automated with high cost in terms of equipment. Even in the clinical chemistry investigation of urine, the question of automation and test simplification plays a special role with respect to reductions in cost. Here, therefore, a forward-looking path for the direction of development of all of clinical chemistry has already been taken for a long time with the development of so-called dry chemistry, especially embodied in the form of test strips.

The determination of the specific weight of urine presented a special problem for the test developer in "dry chemistry" because all the test methods known to date were not transferable to test strips. The development chemists came in useful under the circumstances here, in that the clinical chemist is primarily interested in a statement relating to the concentration of the substances normally contained in the urine. The density is therefore determined by him, because it essentially correlates with the sought-after substance concentration.

Among the substances normally contained in the urine, the salts now again assume a prominent position. It therefore seemed reasonable to determine the salt concentration by means of one of the colligative properties.

A method for determining the specific weight and/or the ionic strength on a test strip is described in U.S. Pat. No. 4,318,709 and the corresponding DE-A-29 44 980. In this method, the sample is mixed with a reagent which contains a weakly acidic or weakly basic, at least 50% neutralized polyelectrolyte polymer and an indicator. The underlying principle is the proportionality between the specific weight and the ionic strength of an aqueous solution.

Polyelectrolyte polymers indicated therein are polymers having ionic groups. Examples which may be mentioned are polyacrylic acid or polyvinylamine.

While the transfer of the osmosis measuring principle (for example U.S. Pat. No. 4,015,462) to test strips obviously comprises technical difficulties, the pH change caused by ions in a buffer system could be measured very easily using a test strip. The buffer system contained complexing buffer substances and ion-exchanging polyelectrolytes. As can be seen from the examples of EP 0 023 631, the essential component for achieving a pH change with increasing ionic strength is the nature and the pH of the buffer substance.

In EP 0 349 934, for example, a method is disclosed which, without using polyelectrolyte polymers, contains at least one pH buffer substance and/or a complexing agent and also a pH indicator as the indicator.

As the previously known methods, for example EP 349 934 and EP 114 315, measure a pH shift caused by salts, pH variations of the urines can only be compensated inadequately by corresponding buffering of the test strips.

The previously known methods also have the disadvantage that the dye, once formed, changes with time and also that the test strips "bleed out". This has the result that the value which is read off for the specific weight after one minute can greatly differ from the value which is read off after two or even five minutes.

If the test is then not carried out by persons specifically trained for this purpose, for example any patient, and the assessment is not always performed at the same time, prescribed by the manufacturer of the strip, this can lead to misinterpretations of the state of health, which have serious consequences.

The use of complexing agents additionally further has the disadvantage that the result indicated essentially depends on the composition of the ions, especially the metal ions, in the sample, as the affinity of the complexing agents for various ions is different. This composition, however, is also exposed to great variations in normal urines.

SUMMARY OF THE INVENTION

The present invention was therefore based on the object of developing a method for determining the ionic strength and/or the specific weight of aqueous liquids, which method develops a constant color signal, is ion-independent and prevents bleeding out of the test strips prepared in accordance with the method.

Surprisingly, it has been found that by addition of detergents to the substances and buffer salts known to the person skilled in the art and used per se as pH indicators, reagents are obtained which do not determine the specific weight indirectly by means of a pH measurement, but directly as a color change which is caused by ion concentration (see Tab. 1) and, as a result of their exceptional color brilliance, possessed a considerably higher sensitivity than those known previously and additionally showed a high color constancy and fastness to bleeding out.

BRIEF DESCRIPTION OF THE DRAWING

FIG. 1 shows the results of a determination of urines having different densities using the reagents of the present invention. The horizontal or X axis DE plots arbitrary units of density.

DETAILED DESCRIPTION

The invention thus relates to a buffered reagent for determining the ionic strength and/or the specific weight of an aqueous liquid with the aid of a color indicator, which reagent contains at least one detergent and a substance known per se as a pH indicator as the indicator and whose pH shift on sample addition is lower than corresponds to the observable color shift.

As indicator, the reagent preferably contains Thymol Blue or Bromothymol Blue.

The detergent used is a quaternary ammonium salt or a mixture of several quaternary ammonium salts.

A zwitterionic detergent or a mixture of zwitterionic detergents is also suitable.

The reagent according to the invention is preferably impregnated onto an absorbent support.

The invention further relates to a method for determining the ionic strength and/or the specific weight of an aqueous liquid, which comprises using a reagent as described above for the determination.

The invention additionally relates to test strips for determining the ionic strength or the specific weight of an aqueous liquid from a plastic strip and an absorbent support attached thereto and impregnated with a reagent, which comprises using the reagent described above as the reagent.

Other constituents can be dissolved and/or not dissolved in the aqueous liquid whose ionic strength, also known as osmolarity, and/or whose specific weight is determined in the method according to the invention. Dissolved constituents are ionic and nonionic substances. Undissolved constituents can be sparingly soluble chemical substances, but also other materials, such as biological substances, for example cells.

The method according to the invention is particularly highly suitable for body fluids, such as perspiration and urine. It has proved particularly suitable for the investigation of urine.

pH buffer substances are substances known to the person skilled in the art. A pH buffer substance is a mixture of a weak acid with a virtually completely dissociated salt of this acid and/or a mixture of a weak base with a virtually completely dissociated salt of this base (see, for example, Römpps Chemie Lexikon (Rompp's Chemical Encyclopedia, 7th edition, volume 5, head word "Buffer"). The pH of the buffer hardly changes on addition of acids or bases.

Preferred buffer substances in the preferred pH range from 4 to 11 are, for example, buffers which contain the following ions: phosphate, borate, carbonate, citrate, diethylmalonate, nitrilo-trismethylenephosphate. Zwitterionic buffers, such as, for example, glycine buffer or 2-(N-morpholino)ethanesulfonic acid (MES) are also suitable. The pH buffer substances are employed in concentrations such that the concentration after addition of the sample is 0.005 to 1.0 mol/l, preferentially 0.08 to 0.3 mol/l, very preferentially 0.10–0.18 mol/l.

Detergents are substances known to the person skilled in the art. The terms detergent and surfactants are synonymous in the sense of this invention (see also Römpps Chemielexikon (Rompp's Chemical Encyclopedia, 7th edition, vol. 6, headword "Surfactants").

Preferred detergents are compounds of the quaternary ammonium salt type (quats) and detergents of the zwitterionic detergent type. In the test composition according to the invention, the detergents are preferentially employed in concentrations of 0.04% to 5% in the impregnation solution. The detergents can also be used for improving the brilliance of test compositions according to the prior art.

The use of detergent mixtures is also preferred.

Suitable indicators for determining the ionic strength or the specific weight of urine are substances known per se as pH indicators for a pH from 4 to 12. Thymol Blue and Bromothymol Blue are particularly highly suitable here.

Preferentially, the concentration of the indicator after addition of the sample is in the range from 0.1 to 100 mmol/l, particularly preferentially 1 to 50 mmol/l.

The reagent according to the invention does not require any addition of polyelectrolyte polymer or complexing agent. The addition of detergents to reagents for determining the ionic strength or the specific weight which contain polyelectrolyte polymers or complexing agents leads, however, to a higher color brilliance in these reagents and is therefore also part of this invention.

The method according to the invention can be carried out both in solution and in a matrix-like support material.

The preferred embodiment of the method is that in which the reagent is expediently applied as a coating to an absorbent support on a test strip. Preferred supports are porous support materials or mats. Mats are understood as meaning paper-like supports made of fibers. Absorbent supports impregnated with reagent are preferably prepared by impregnating the absorbent support material with a solution of the reagent and drying it. A reagent film is by this means formed on the entire surface, preferably even the inner surface. The reagent can also be applied to a support, for example directly to the test strips, with film-forming and swellable additives. The reagents can also contain customary additives, such as, for example, stabilizers, wetting agents or swelling agents.

In the preferred embodiment of the method according to the invention, these test strips have a test area which consists of a mat impregnated with a solution of the reagent and dried. The test area is brought into contact with the urine to be investigated, for example by dipping the test strip into the urine and taking it out as soon as the test area is wet. The color which the test area has then taken is compared with the color of a sample attached to the test strip. Each color of the sample here is allocated a value for a specific weight. The specific weight to be determined has the value which is allocated to the sample having a matching color.

In a particularly preferred embodiment, the test area for determining the ionic strength or the specific weight is a constituent of a multiple strip known per se to the person skilled in the art.

The reading off and assessment of the test area in an instrument such as is known, for example, under the name RapimatR (Behringwerke AG, Marburg, Germany) is preferred.

A preferred embodiment of the reagent to be used for impregnation can, for example, have the following composition:

Buffer: Phosphate buffer pH 7–8, preferentially 7.5 in a final concentration of 80–300 mmol/l.

Detergent: Zwitterionic detergents, preferentially benzethonium chloride 0.2–2% (w/v), preferentially 1%.

Indicator: pH indicator having a color change from pH 7 to 9, preferentially Thymol Blue or Bromothymol Blue in a concentration of 1–50 mmol/l, preferentially 5–20 mmol/l.

The assessment in the method according to the invention can be carried out in a manner known per se by means of a calibration curve. In the case of visual assessment, this calibration curve is, for example, a color scale.

The assessment of a determination by the method according to the invention can already be carried out after 60 sec; the resulting color is then stable over a period of at least 15 min, so that even, for example, in relatively long series of measurements the values determined are still directly comparable.

Claims and examples are part of the disclosure.

The following examples serve to illustrate the invention and do not restrict this in any manner.

EXAMPLE 1

Paper from Machery+Nagel (N 8.18.) is impregnated with the following solution and dried:

1 g of benzethonium chloride (Serva) is dissolved in 90 ml of 90 mM sodium dihydrogenphosphate solution pH about 7.5. After addition of 10 ml of a 1.5% strength methanolic Bromothymol Blue solution, the mixture is adjusted to pH 7.5 with 1 M sodium hydroxide solution. The test paper thus obtained is cut up into squares of size 5×5 mm and glued onto stiff plastic, film. In this manner, test strips are obtained which, after dipping into various concentrated urines, can be assessed visually and by reflection photometry. The results are shown in the table below:

A) Visual Assessment:

TABLE 1

| Twice-distilled | Sodium chloride solution having the following specific weight | | |
|---|---|---|---|
| | 1.005 | 1.010 | 1.020 |
| water | | | |
| Green-blue | Bluish green | Green | Pale green |
| Native urine adjusted with sodium chloride to the following specific weights | | | |
| Without addition 1.018 | 1.024 | 1.030 | 1.040 |
| Green | Green | Greenish Yellow | Yellow |

B) Assessment Using an Automatic Apparatus

The test strips prepared as described above were assessed (FIG. 1) completely automatically, after dipping into the urines to be investigated, in an instrument suitable for this purpose (RapimatR, Behringwerke AG, Germany). The urines used were clinical urine samples (X) which were diluted 1+1 with distilled water for the lower density range ( ). The density unit was defined as $$DU = (\text{measured density} - 1,000) \times 103$$

EXAMPLE 2

Comparison with the Prior Art

A solution according to Example 1 containing 120 mmol/l of buffer, instead of 90 mmol/l of buffer, was measured before and after addition of the sample with the aid of a pH electrode. The relative pH changes in relation to the respective starting solutions, which were mixed with a corresponding volume of distd. water, are given in the Table:

Appropriate reagents were prepared according to EP 349 934/Example 1 and EP 114 315/Example 9.1 and tested as described above.

| Sample | Density | Example 1 | EP 349 934 | EP 114 315 |
|---|---|---|---|---|
| H2O | 1.000 | 0.00 | 0.00 | 0.00 0.4 |
| mol/l | 1.017 | 0.10 | 0.30 | 0.40 NaCl |
| Normal urine | 1.017 | 0.00 | 0.15 | 0.50 |

What is claimed is:

1. A reagent composition for directly measuring ionic strength and/or specific gravity of a sample of an aqueous liquid, said reagent composition consisting essentially of:
   (a) one or more pH buffers having a pH of 4 to 11;
   (b) one or more indicators selected from the group consisting of pH indicators; and
   (c) one or more surfactants wherein a pH shift on sample addition is lower than that which corresponds to an observable color shift of the one or more pH indicators so that a color change of the one or more pH indicators is essentially directly dependent on the ionic strength and/or specific gravity of the sample and not on a shift in pH of the reagent composition upon addition of the sample of aqueous liquid thereto.

2. The reagent as claimed in claim 1, wherein the pH indicator is Thymol Blue or Bromothymol Blue.

3. The reagent as claimed in claim 1, wherein the surfactant contains one or more quaternary ammonium salts.

4. The reagent as claimed in claim 1, wherein the surfactant contains one or more zwitterionic detergents.

5. The reagent as claimed in claim 1, which is impregnated onto an absorbent support.

6. A method for determining the ionic strength and/or the specific weight of an aqueous liquid, comprising the steps of
   (i) bringing the liquid into contact with the reagent composition as claimed in claim 1 to form a mixture,
   (ii) determining the color shift of the resulting mixture, and
   (iii) determining the ionic strength and/or the specific weight of the liquid from the color shift.

7. The method as claimed in claim 6, wherein a calibration curve is used for determining the ionic strength and/or the specific weight.

8. The method as claimed in at least one of claims 6 or 7, wherein the reagent is impregnated onto an absorbent support.

9. A test strip for determining the ionic strength and/or the specific weight of an aqueous liquid comprising a plastic strip and an absorbent support attached thereto which is impregnated with the reagent composition as claimed in claim 1.

10. A buffered reagent for determining the ionic strength or the specific weight of an aqueous liquid with the aid of a color indicator, which reagent contains in aqueous solution at least one detergent, wherein said detergent is an anionic, nonionic or zwitterionic detergent, one buffer and one pH indicator wherein a pH shift on sample addition is lower than that which corresponds to an observable color shift of the pH indicator so that a color change of the pH indicator is directly dependent on the ionic strength and/or specific gravity of the aqueous liquid and not on a shift in pH of the buffered reagent upon addition of the aqueous liquid thereto.

11. The buffered reagent of claim 10 wherein said at least one detergent is present in an amount from 0.04% to 5% (w/v), said buffer is present in an amount from 0.005 to 1.0 mol/l, and said pH indicator is present in an amount from 0.1 to 100 mMol/l.

12. A method for determining the ionic strength or the specific weight of an aqueous liquid comprising the steps of:
   (i) bringing the liquid into contact with a buffered reagent for determining the ionic strength or the specific weight of an aqueous liquid with the aid of a color indicator to form a mixture, which reagent contains an aqueous solution of at least one detergent, wherein said detergent is an anionic, nonionic or zwitterionic detergent, one buffer, and one pH indicator, wherein a pH shift on sample addition is lower than that which corresponds to an observable color shift of the pH indicator so that a color change of the pH indicator is directly dependent on the ionic strength and/or specific gravity of the aqueous liquid and not on a shift in pH of the buffered reagent upon addition of the aqueous liquid thereto; and
   (ii) determining a color shift of the resulting mixture.

13. The method of claim 12 wherein said at least one detergent is present in an amount from 0.04% to 5% (w/v), said buffer is present in an amount from 0.005 to 1.0 mol/l, and said pH indicator is present in an amount from 0.1 to 100 mMol/l.

14. The method of claim 13 wherein said reagent is impregnated onto an absorbent support.

15. The method of claim 12 wherein said reagent is impregnated onto an absorbent support.

16. A test strip for determining the ionic strength or the specific weight of an aqueous liquid comprising an absorbent support impregnated with a buffered reagent for determining the ionic strength or the specific weight of an aqueous liquid with the aid of a color indicator, which reagent contains an aqueous solution of at least one detergent, wherein said detergent is an anionic, nonionic or zwitterionic detergent, one buffer, and one pH indicator, wherein a pH shift on sample addition is lower than that which corresponds to an observable color shift of the pH indicator so that a color change of the pH indicator is directly dependent on the ionic strength and/or specific gravity of the aqueous liquid and not on a shift in pH of the buffered reagent upon addition of the aqueous liquid thereto.

17. The test strip of claim 16 wherein the at least one detergent is present in an amount from 0.04% to 5% (w/v), said buffer is present in an amount from 0.005 to 1.0 mol/l, and said pH indicator is present in an amount from 0.1 to 100 mMol/l.

* * * * *